United States Patent [19]

Fields

[11] 4,108,864

[45] Aug. 22, 1978

[54] TRICYCLOUNDECENE-1,2,3,4,9,9-HEXA-HALO-5,6-DIACYL COMPOUNDS

[75] Inventor: Ellis K. Fields, River Forest, Ill.

[73] Assignee: Standard Oil Company a corporation of Indiana, Chicago, Ill.

[21] Appl. No.: 744,335

[22] Filed: Nov. 23, 1976

[51] Int. Cl.² .................. C07C 61/12; C07D 209/94; C07D 307/93
[52] U.S. Cl. ........................... 260/326 C; 260/295 F; 260/346.3; 260/346.6; 260/501.15; 260/514 G; 260/544 F; 260/544 L; 260/557 B; 560/117
[58] Field of Search ............. 260/346.3, 346.6, 295 F, 260/326 C, 501.15, 514 G, 544 F–544 L, 557 B; 560/117

[56] References Cited

U.S. PATENT DOCUMENTS

| 3,152,172 | 10/1964 | Roberts et al. ............... 260/346.3 X |
| 3,419,576 | 12/1968 | Roberts et al. ............... 260/326 C |
| 3,474,136 | 10/1969 | Dunkel et al. ............... 260/557 B X |

OTHER PUBLICATIONS

Sandermann et al., Chemical Abstracts, vol. 73 (1970) 109,934r.

*Primary Examiner*—Richard L. Raymond
*Attorney, Agent, or Firm*—William C. Clarke; Arthur G. Gilkes; William T. McClain

[57] ABSTRACT

Tricycloundecene-1,2,3,4,9,9-hexahalo-5,6-diacyl compounds.

13 Claims, No Drawings

TRICYCLOUNDECENE-1,2,3,4,9,9-HEXAHALO-5,6- DIACYL COMPOUNDS

This invention relates to tricycloundecene-1,2,3,4,9,9-hexahalo-5,6-diacyl compounds. More particularly, this invention relates to tricycloundecene-1,2,3,4,9,9-hexahalo-5,6-dicarboxylic acids, tricycloundecene-1,2,3,4,9,9-hexahalo-5,6-anhydrides, tricycloundecene-1,2,3,4,9,9-hexahalo-5,6-dicarboxylic acid alkali, alkaline earth salts and amine salts, tricycloundecene-1,2,3,4,9,9-hexahalo-5,6-dicarboxylic acid esters and acid halides.

This invention relates to 1,2,3,4,9,9-hexachloro-1,4,4a,5,6,8a-hexahydro-1,4-methanonaphthalene-5,6-dicarboxylic acid compounds, 1,2,3,9,9-hexachloro-1,4,4a,5,8,8a-hexahydro-1,4-methanonaphthalene-5,6-dicarboxylic acid compounds and 1,2,3,4,9,9-hexachloro-1,4,4a,7,8,8a-hexahydro-1,4-methanonaphthalene-5,6-dicarboxylic acid compounds as new compositions of matter. The structures of these compounds are:

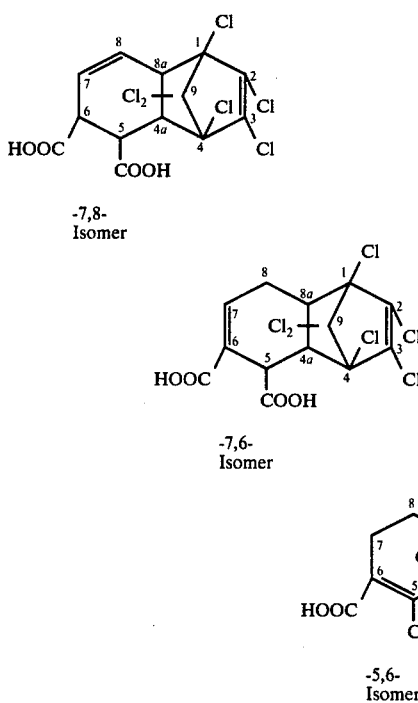

For convenience these compounds are referred to hereinafter as tricycloundecene-1,2,3,4,9,9-hexahalo-5,6-dicarboxylic acid or diacyl compounds. These compounds possess high toxicity to fungicidal growths and can be converted to amine salts for use in oils as an extreme pressure agent. They can also be used for preparing fire-resistant resins and as plasticizers.

The object of this invention accordingly is to provide a new class of difunctional acyl compounds. Another object is to provide new pesticidal compounds which possess a molecular configuration that allows the preparation of water-soluble derivatives. Another object is to provide monomers for fire-resistant resins. Another object is to provide a chlorine compound suitable for use as an extreme pressure additive to impart high film strength to lubricating oils of many types, i.e. cutting oils, gear oils, and greases, etc. Other objects appear hereinafter.

For purposes of this invention, the term "acyl" is used in a generic sense to include carbacyl compounds, such as free acids,

acid salts, esters, acyl halides, amides, imides, anhydrides, etc.

I have now found it possible to produce a new class of difunctional acyl compounds. These compounds are tricycloundecene hexahalo compounds having acyl functionality in two positions on the tricycloundecene nucleus. As indicated above, these compounds can be used to produce alkyds, amide-imides, polyamides, plasticizers, oil additives, etc.

In oversimplified form, these compounds can be viewed as Diels-Alder adducts of the corresponding dihydrophthalic acid derivatives. However, as explained below, only the tricycloundecene hexahalo diacid salts are formed initially and the other tricycloundecene diacid derivatives are preferably produced from the acid salts. These diacid salts have the structures

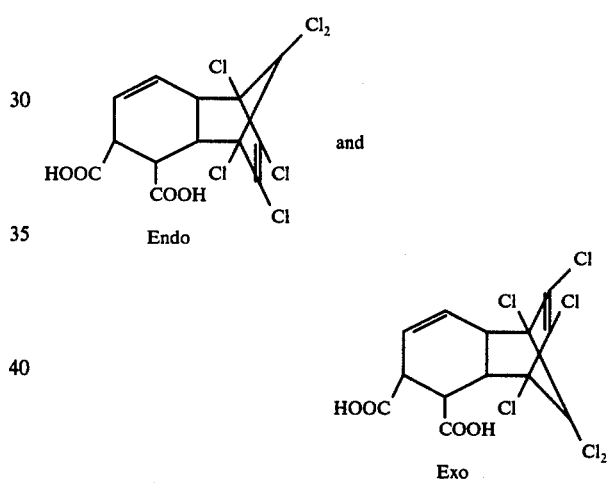

It is believed that the endo form is predominant.

Broadly speaking, the tricycloundecene hexahalo dicarboxylic acids are produced by mixing the 1,2- or 1,4-dihydrophthalic acids or anhydrides with hexahalocyclopentadiene (hexachlorocyclopentadiene or hexabromocyclopentadiene) in mole ratios of 1:1 to 1:3. This mixture is heated at a temperature of about 100° to 200° C either under reflux conditions or in a pressure reactor. In general, it is preferred to carry out the reaction at 130° to 160° C. The reaction can be carried out for about 2 to 60 hours or more. Other things being equal, the longer the reaction time, the better the yield. After the Diels-Alder reaction is completed, the tricycloundecene hexahalodicarboxylic acid can be solvent extracted with a hydrocarbon solvent and further purified with a caustic aqueous solution.

The double bond in the 7,8 position can be forced into the 6,7 or 5,6 position by heating the tricycloundecene hexahalo acyl compound in the presence of a strong alkali such as sodium hydroxide at a temperature of 20° to 100° C for 1 to 24 hours. The -5,6-, -6,7- and -7,8- double bond compounds represent stable configurations and the compounds accordingly remain so. Similarly, the starting material of 1,2-dihydrophthalic acid can be driven to the 1,4-dihydrophthalic acid by heating alone or in alkali at 20° to 100° C for 1 to 24 hours. The 1,4 is the more stable isomer of the two and the product remains so.

The 1,2-dihydrophthalic acid compound can be made in high yields by electrochemical reduction of phthalic acid. As stated above, upon prolonged heating under basic conditions, 1,2-dihydrophthalic acid isomerizes to 1,4-dihydrophthalic acid. The anhydrides of 1,2- and 1,4-dihydrophthalic acid are formed by refluxing with acetic anhydride at a temperature within the range of about 100° to 300° C. In general, it is preferred to carry out the reaction at 110° to 150° C, particularly when acetic anhydride is at least one component of the solvent. The reaction can be carried out for about 1 to 100 hours. Dimerization does not usually take place. Suitable solvents for ring closure include organic acid anhydrides, such as acetic anhydride, propionic anhydride, acetic anhydride/acetic acid mixed solvents, organic acids which promote ring closure, such as trifluoroacetic acid, trifluoroacetic acid/acetic acid mixed solvent, etc.

The hexahalocyclopentadiene compound is defined as having six halogen atoms which can be fluorine, chlorine, bromine or iodine. Chlorine and bromine are preferred because of availability and low cost.

The anhydride ring of the tricycloundecene hexahalo anhydride, produced in any manner, can be opened by heating from 40° to 100° C the anhydride in a 1 to 50%, preferably 20 to 30%, by weight aqueous dispersion until the solid dissolves. The tricycloundecene hexahalo dicarboxylic acid cannot be isolated by driving off water as the dicarboxylic acid anhydride tends to reform. If desired the alkali metal salts (sodium, potassium, etc. or alkaline earth metal salts can be formed by mixing the anhydride with the appropriate aqueous hydroxide (sodium hydroxide, calcium hydroxide, etc.) or by neutralizing the aqueous tricycloundecene hexahalo dicarboxylic acid composition with sodium hydroxide, potassium hydroxide, ammonium hydroxide, tetramethyl ammonium hydroxide, pyridine, etc.

The tricycloundecene hexahalo anhydrides can be converted to amides by dispersing or dissolving the tricycloundecene hexahalo anhydride in a suitable nitrogen containing medium, such as aqueous ammonium hydroxide, liquid or aqueous solution of primary amines (methylamine, ethylamine, aniline, etc.) or liquid or aqueous solutions of secondary amines (dimethylamine, diethylamine, N-methylaniline) etc., and heating to open the anhydride ring. Usually one carboxy group of the anhydride is converted initially to the amide form and the other carboxy group is converted to a carboxylate/salt form, i.e. half-amide. Under anhydrous conditions, continued heating of half-amides containing at least one active Zerwittinoff hydrogen bonded to nitrogen convert one of the half-amide groups to the imide. If desired polyamines containing at least one primary or secondary amine group, such as ethylene diamine, diethylene triamine, propylene diamine, N,N'-dimethyl ethylene diamine, etc., can be used in place of the simple primary and secondary amines.

The tricycloundecene hexahalo diesters can be formed by reacting the tricycloundecene hexahalo anhydrides, half-anhydrides or diacids with at least 2 moles of an appropriate monohydroxy compound per mole tricycloundecene hexahalo compound at from 50° to 200° C. using a conventional esterification catalyst.

Suitable monohydroxy compounds include alcohols containing from 1 to 24 carbon atoms such as methyl alcohol, ethyl alcohol, isopropyl alcohol, allyl alcohol, methallyl alcohol, n-butyl alcohol, n-hexyl alcohol, n-octyl alcohol, 2-ethylhexyl alcohol, decyl alcohol, tridecyl alcohol, stearyl alcohol, oleyl alcohol, tetracosyl alcohol; aromatic hydroxy compounds containing 6 to 24 carbon atoms, such as phenol, cresol, para-stearyl phenol, naphthol, etc. In general, the reaction vessel should contain from about 1 to 10 moles of monohydroxy compound per carboxyl equivalent in said tricycloundecene compound.

Suitable esterification catalysts include sulfuric acid, phosphoric aid, para-toluene sulfonic acid, benzene sulfonic acid, stannous octoate, etc. In general, the acid catalyst can comprise from about .01 to 5 parts by weight per 100 parts by weight of tricycloundecene hexahalo compound.

In somewhat greater detail the esters can be formed by dissolving the tricycloundecene hexahalo compound in from about 1 to 10 moles of monohydroxy compound per carboxyl equivalent in said tricycloundecene compound. One or more monohydroxy compounds can be used to form symmetrical diesters or mixed esters. If desired, a diluent such as xylene or toluene may also be added to aid in the entrainment of water of esterification and to promote the esterification reaction. Either before or after the polycarboxylic acid is dissolved in a monohydroxy compound, a suitable concentration of esterification catalyst is added to the reactor.

The esterification mixture is then heated to a temperature of 50° to 200° C. either under pressure or under suitable reflux conditions for a period of time to complete the esterification. After the esterification is completed, the solution of ester in monohydroxy compound and/or diluent can be isolated by conventional means.

The tricycloundecene hexahalo diesters are excellent plasticizers for resinous polymers of vinyl chloride. These esters can be used in a concentration of from about 5–300 parts by weight per 100 part by weight resinous polymer of vinyl chloride, i.e. in a plasticizing concentration. They may be used as the sole plasticizers, two or more esters may be employed together or alternatively, these esters may be used in conjunction with other conventional plasticizers such as dioctylphthalate, trioctylphosphite, epoxidized glyceride oils, etc.

The tricycloundecene hexahalo diester plasticizers include dialkyl esters of tricycloundecene dicarboxylic acid containing from 1 to 24 carbon atoms in the alkyl groups, preferably 3 to 13 carbon atoms, diaryl ester containing from 6 to 24 carbon atoms in the aryl groups; diaralkyl esters containing from 7 to 24 carbon atoms in the aralkyl groups; dialkenyl esters containing from 3 to 24 carbon atoms, etc. mixed esters containing residues of two types, etc. Suitable esters include the dimethyl ester, diethyl ester, diallyl ester, di-n-butyl ester, di-n-octyl ester, di-2-ethylhexyl ester, ditridecyl ester, dioctadecyl ester, di-tetracosyl ester, allyl 2-ethylhexyl ester, diphenyl ester, dibenzyl ester, di-(p-cresyl)ester, benzyl n-octyl ester, di-(p-octadecylphenyl) ester, etc.

For the purpose of this invention the term "resinous polymer of vinyl chloride" includes homopolymers of vinyl chloride, copolymers of vinyl chloride and vinyl acetate, such as the conventional 95-5 vinyl chloride/vinyl acetate copolymers, partially hydrolyzed vinyl chloride/vinyl acetate copolymers, vinyl acetate/vinyl chloride/alpha, beta-ethylenically unsaturated-alpha, beta-dicarboxylic acid copolymers (such as the butyl half ester of maleic acid or dioctyl fumarate ester, etc.), where in at least 50 mole percent of the polymer constitutes vinyl chloride units.

The plasticized resinous polymers of vinyl chloride can be compounded with stabilizers, such as the organotins, barium/cadmium soaps, polyhydric alcohols, etc.; lubricants, such as fatty acids; pigments, such as zinc oxide, antimony oxide, etc. and fabricated by conventional means into films, sheets, fibers, tubes, etc.

The following examples are merely illustrative.

EXAMPLE I

A mixture of 3.36g (0.02 mole) of 1,2-dihydrophthalic acid and 10 ml. hexachlorocyclopentadiene (0.0574 mole) was heated at 160° C. for 46 hours. The product was dissolved in a mixture of benzene:ether 1:3: the filtered solution was extracted with 10% aqueous potassium hydroxide, and the aqueous solution was separated and acidified. The precipitated oil was taken up in benzene:ether 1:3, the solution was dried, filtered through a bed of charcoal, and evaporated to give 6g. (68 mole % yield) of a very viscous, light orange oil, 1,2,3,4,9,9-hexachloro-1,4,4a,5,6,8a-hexahydro-1,4-methanonaphthalene-5,6-dicarboxylic acid.

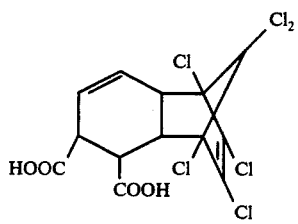

Analysis: Calculated for $C_{13}H_6Cl_6O_4$: Cl, 48.5%; acidity, 255 mg. Found: Cl, 48.1%; acidity, 248 mg. KOH/g The new compound was tested against Late Blight of tomatoes and Leaf Rust of wheat and found effective in protectant control at concentrations 250 ppm and higher.

EXAMPLE II

The di-n-butyl ester of the di-acid product of Example I is prepared in the following procedure. A mixture of 4.3g. (10 mmoles) of diacid, Example I, 9.15 ml. (100 mmoles) of n-butanol, 10.62 ml. (100 mmoles) of toluene, and 1 ml. of p-toluenesulfonic acid is refluxed at 115° C in a flask equipped with a Stark and Dean trap to remove water. After 6 hours, no more water is formed. The mixture is cooled, diluted with 50 ml. of ether, washed with cold 5% potassium carbonate solution to remove any acid, dried over 5g. Drierite, filtered, and the filtrate is evaporated at 80° C and 0.2 Torr in a rotary evaporator to give the di-n-butyl ester of structure II, 1,2,3,4,9,9-hexachloro-1,4,4a,5,6,8a-hexahydro-1,4-methanonaphthalene-5,6-dicarboxylic acid, n-butyl ester:

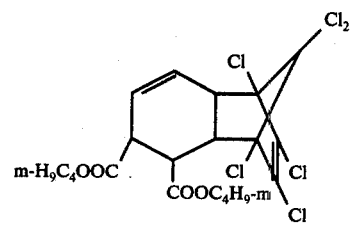

The yield is 5.36 g., 97.3 mole% of light yellow, very viscous liquid, whose elemental analysis corresponds to the compound of structure II.

EXAMPLE III

The anhydride of the diacid product of Example I is prepared by this procedure: a mixture of 8.6g. (20 mmoles) of diacid, Example I, and 9.375 ml. (100 mmoles) of acetic anhydride is refluxed for 4 hours at 140° C. Acetic acid and excess acetic anhydride are removed at 100° C and 0.2 Torr in a rotary evaporator to give the anhydride of structure III, 1,2,3,4,9,9-hexachloro-1,4,4a,5,6,8a-hexahydro-1,4-methanonaphthalene-5,6-dicarboxylic acid anhydride:

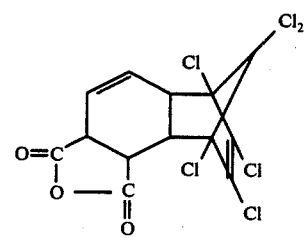

The yield is 8.24g, quantitative, of anhydride, a light yellow, viscous liquid whose elemental composition corresponds to the compound of structure III.

EXAMPLE IV

The half-amide of the di-acid of Example I is prepared by stirring a mixture of 8.24g. (20 mmoles) of anhydride of Example III with 56.67 ml. (100 mmoles) of 30% aqueous ammonia at 20° C until the anhydride dissolves and a clear solution is obtained. The solution is warmed to 40° C and blown with nitrogen at 1000 cc/minute to drive off the excess ammonia for 2 hours, cooled to 20° C and acidified with 2.67 ml. (50 mmoles) of sulfuric acid in 50 ml. of water. The acid amide of structure IVa, 1,2,3,4,9,9-hexachloro-1,4,4a,5,6,8a-hexahydro-1,4-methanonaphthalene-5-carboxylic acid-6-carboxylic acid amide, and IVb, 1,2,3,4,9,9-hexachloro-1,4,4a,5,6,8a-hexahydro-1,4-methanonaphthalene-5-carboxylic acid amide-6-carboxylic acid, are

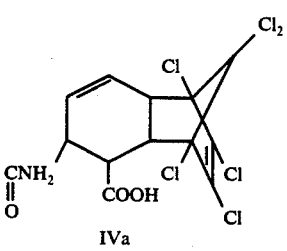

IVa

-continued

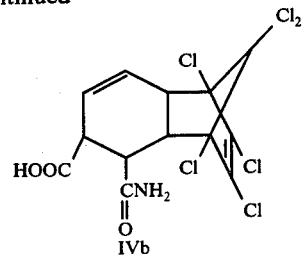

IVb precipitated as a low-melting yellow solid, yield 8.5g, 99 mole %, whose elemental analysis corresponds to the compound of structures IVa and IVb.

EXAMPLE V

The imide of structure V

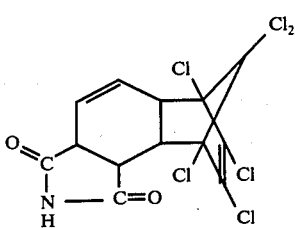

V is prepared by heating 4.29g (10 mmoles) of the amide of Example IV at 200°-230° C at 0.2 Torr for 1 hour. The yield is 4.0g. (97 mole %) of low-melting yellow imide whose elemental analysis corresponds to the compound of structure V, 1,2,3,4,9,9-hexachloro-1,4,4a,5,6-,8a-hexahydro-1,4-methanonaphthalene-5,6-dicarboxylic acid imide.

I claim:

1. A tricycloundecene-1,2,3,4,9,9-hexahalo-5,6-diacyl compound selected from the group consisting of 1,2,3,4,9,9-hexahalo-1,4,4a,5,6,8a-hexahydro-1,4-methanonaphthalene-5,6,-dicarboxylic acid compounds, 1,2,3,4,9,9-hexahalo-1,4,4a,5,8,8a-hexahydro-1,4,-methanonaphthalene-5,6-dicarboxylic acid compounds and 1,2,3,4,9,9-hexahalo-1,4,4a,7,8,8a-hexahydro-1,4-methanonaphthalene-5,6-dicarboxylic acid compounds wherein the said acid compounds are selected from the group consisting of free acids and acid salts, esters, acyl halides, amides, imides, and anhydrides thereof.

2. The compound of claim 1 wherein the said tricycloundecene-1,2,3,4,9,9-hexachloro-5,6-diacyl compound is 1,2,3,4,9,9-hexachloro-1,4,4a,5,6,8a-hexahydro-1,4-methanonaphthalene-5,6-dicarboxylic acid.

3. The compound of claim 1 wherein the said tricycloundecene-1,2,3,4,9,9-hexachloro-5,6-diacyl compound is 1,2,3,4,9,9-hexachloro-1,4,4a,5,8,8a-hexahydro-1,4-methanonaphthalene-5,6-dicarboxylic acid.

4. The compound of claim 1 wherein the said tricycloundecene-1,2,3,4,9,9-hexachloro-5,6-diacyl compound is 1,2,3,4,9,9-hexachloro-1,4,4a,7,8,8a-hexahydro-1,4-methanonaphthalene-5,6-dicarboxylic acid.

5. The compound of claim 1 wherein said tricycloundecene-1,2,3,4,9,9-hexahalo-5,6-diacyl compound is a diester of a monohydroxy compound containing 1 to 24 carbon atoms.

6. The compound of claim 5 wherein the said diester is 1,2,3,4,9,9-hexachloro-1,4,4a,5,6,8a-hexahydro-1,4-methanonaphthalene-5,6-dicarboxylic acid, n-butyl ester.

7. The compound of claim 1 wherein said tricycloundecene-1,2,3,4,9,9-hexahalo-5,6-diacyl compound is a tricycloundecene-1,2,3,4,9,9-hexahalo-5,6-dicarboxylic acid anhydride.

8. The compound of claim 7 wherein the said anhydride is 1,2,3,4,9,9-hexachloro-1,4,4a,5,6,8a-hexahydro-1,4-methanonaphthalene-5,6-dicarboxylic acid anhydride.

9. The compound of claim 1 wherein said tricycloundecene-1,2,3,4,9,9-hexahalo-5,6-diacyl compound is a half-amide.

10. The compound of claim 9 wherein the said half amide is 1,2,3,4,9,9-hexachloro-1,4,4a,5,6,8a-hexahydro-1,4-methanonaphthalene-5-carboxylic acid-6-carboxylic acid amide.

11. The compound of claim 9 wherein the said half amide is 1,2,3,4,9,9-hexachloro-1,4,4a,5,6,8a-hexahydro-1,4-methanonaphthalene-5-carboxylic acid amide-6-carboxylic acid.

12. The compound of claim 1 wherein said tricycloundecene-1,2,3,4,9,9-hexahalo-5,6-diacyl compound is an imide.

13. The compound of claim 12 wherein the said imide is 1,2,3,4,9,9-hexachloro-1,4,4a,5,6,8a-hexahydro-1,4-methanonaphthalene-5,6-dicarboxylic acid imide.

* * * * *